United States Patent [19]
Dennis et al.

[11] Patent Number: 6,143,325
[45] Date of Patent: Nov. 7, 2000

[54] NEFAZODONE DOSAGE FORM

[75] Inventors: Andrew B. Dennis; Peter Timmins, both of Wirral; Alison C. Hodsdon, St. Leonard's-on-Sea, all of United Kingdom

[73] Assignee: Bristol-Myers Squibb Company, Princeton, N.J.

[21] Appl. No.: 09/299,959

[22] Filed: Apr. 26, 1999

Related U.S. Application Data

[60] Provisional application No. 60/088,211, Jun. 5, 1998.

[51] Int. Cl.$^7$ .............................. A61K 9/22; A61K 9/28; A61K 31/495; A61K 31/4196
[52] U.S. Cl. ..................... 424/468; 424/464; 424/474; 424/480; 514/252; 514/255.03; 514/384
[58] Field of Search .................. 514/252.12, 255.03, 514/384; 424/468, 464, 474, 480

[56] References Cited

U.S. PATENT DOCUMENTS

| | | |
|---|---|---|
| 4,792,452 | 12/1988 | Howard et al. . |
| 5,169,638 | 12/1992 | Dennis et al. ............................ 424/457 |
| 5,431,922 | 7/1995 | Nicklasson . |
| 5,536,507 | 7/1996 | Abramowitz et al. ................... 424/479 |

FOREIGN PATENT DOCUMENTS

WO 97/47285  12/1997  WIPO .

OTHER PUBLICATIONS

Keller, "Moderni Approcci Al Trattamento Dell'Ansia Associata Alla Depressione," *Rivista Di Psichiatria*, vol. 31, No. 1, Jan. 1, 1996, pp. 18–21.

Nutt, "Early Action of Nefazodone in Anxiety Associated with Depression," *J. Psychopharmacol (Oxford)*, 1996, 10, Suppl. 1, pp. 18–21.

Kuzel, et al., "Treating Comorbid Depression and Anxiety," *Journal of Family Practice*, 1996, 43/6, Suppl. (S45–S53).

Zajecka, "The Effect of Nefazodone on Comorbid Anxiety Symptoms Associated with Depression: Experience in Family Practice and Psychiatric Outpatient Settings," *Journal of Clinical Psychiatry*, vol. 57, Jan. 1, 1996, pp. 10–14.

Fawcett, et al., "Response of Anxiety and Agitation Symptoms During Nefazodone Treatment of Major Depression," *Journal of Clinical Psychiatry*, vol. 56, No. 6, Jan. 1, 1995, pp. 37–42.

Berkow and Fletcher (eds.), *Merck Manual of Diagnosis and Therapy*, 1987, Merck Sharp & Dohme Research Laboratories, Rahway, NJ, pp. 1507–1508.

Goldberg, "Diagnostic Dilemmas Presented by Patients with Anxiety and Depression," *American Journal of Medicine*, vol. 98, No. 3, Mar. 1, 1995, pp. 278–284.

*Primary Examiner*—Thurman K. Page
*Assistant Examiner*—Amy E Pulliam
*Attorney, Agent, or Firm*—Richard P. Ryan

[57] ABSTRACT

Extended-release nefazodone compositions containing nefazodone hydrochloride, ionic and non-ionic gelling polymers, an insoluble hydrophilic agent, and optional pharmaceutically acceptable excipients demonstrate pH-modulated release of nefazodone. These compositions are formulated into unit dosage forms for improved oral administration. The improvements comprise an extended drug release profile providing comparative levels of nefazodone with respect to immediate release dosage forms and, additionally, demonstrating the lack of a food effect.

25 Claims, No Drawings

NEFAZODONE DOSAGE FORM

CROSS REFERENCE TO RELATED APPLICATION

This application is a continuation-in-part of U.S. Ser. No. 60/088,211 provisionally filed Jun. 5, 1998.

FIELD OF THE INVENTION

The invention relates to an extended-release formulation, preferably in the form of a tablet or other oral dosage form, for slowly releasing the medicinal agent, nefazodone.

BACKGROUND OF THE INVENTION

Nefazodone (SERZONE®), 2-[3-[4-(3-chlorophenyl)-1-piperazinyl]-propyl-]5-ethyl-2,4-dihydro-4-(2-phenoxyethyl)-3H-1,2,4-triazol-3-one hydrochloride is a novel antidepressant chemically unrelated to tricyclic or tetracyclic antidepressants and the selective serotonin uptake inhibitors in current use. Its activity appears to be linked to the potentiation of serotonergic activity in vivo as it blocks serotonin 5-HT$_2$ receptors and reversibly inhibits serotonin re-uptake. It does not inhibit monoamine oxidase and exhibits decreased anticholinergic, antihistamine, alpha-adrenergic and sedative activity relative to tricyclic antidepressants.

Currently nefazodone hydrochloride is available in the form of immediate-release tablets, which have to be dosed twice daily. Multiple (two or more) step titration to an effective dose is often needed to allow administration of a clinically effective dose while allowing development of tolerance to the serotonergic effects of the drug that some patients find uncomfortable during the initiation of treatment with nefazodone. A once daily formulation that (relative to equivalent doses of the immediate-release formulation) reduced or "blunted" plasma peak levels but still provided for appropriate exposure to the drug (similar area under the plasma drug concentration-time curve compared to equivalent doses of the drug given twice a day as the currently available immediate-release formulation) is very desirable.

There are several difficulties associated with the formulation of a nefazodone product for oral administration that allows the reliable prolonged delivery of drug required to permit once daily dosing. These are:

drug metabolism drug solubility total daily dose

Drug metabolism

Nefazodone exhibits a significant first-pass metabolism, with the result that the immediate-release tablets show a bioavailability of approximately 20% and significant levels of three pharmacologically-active metabolites, a triazoledione, hydroxynefazodone and m-chlorophenylpiperazine (mCPP). (1,2) It is often the case that extended-release of drugs subject to a first pass metabolism results in an increase in the extent of metabolism. Highly metabolized drugs are thus often considered inappropriate candidates for formulation as extended-release systems (3).

It has been suggested that the metabolite mCPP may be responsible for some of the undesirable effects associated with nefazodone administration. Nefazodone is in fact generally regarded as a well-tolerated drug when given in clinically effective doses of up to 450 mg three times a day. The metabolite mCPP is a partial agonist at the 5-HT$_{2B}$ and 5-HT$_{2C}$ receptors and has some activity, usually seen as antagonist activity, at 5-HT$_{2A}$ receptors (4,5,6,7). In rodents it has anxiogenic-like properties, causes hypoactivity, hypophagia, oral dyskinesia, penile erection and hyperthermia (8,9). A dose-dependent hypoglycemic effect of mCPP mediated through 5-HT$_{2C}$ or 5HT$_{2B}$ receptors is seen in rats (10). It has been shown to increase anxiety in humans (and can cause panic attacks), may precipitate migraine attacks in those susceptible to such attacks, can disrupt sleep, be hypophagic in humans also and may have psychotogenic effects (9). As many of these effects are antagonistic to the beneficial effects of nefazodone, and because some of the described effects of mCPP are reminiscent of some of the adverse effects of nefazodone, an objective of this invention would be to sustain release of the drug substance without increasing the amount of this metabolite produced relative to that seen with the immediate-release formulation following oral administration of the drug.

Nefazodone exhibits non-linear kinetics, with the observed increase in nefazodone plasma concentrations being greater than would be expected if they were proportional to the increase in dose (11). Nefazodone is metabolized by and also inhibits cytochrome P450 (CPY) 3A4. This isozyme is also responsible for the further metabolism of the triazoledione and hydroxynefazodone. Nefazodone is also a weak inhibitor of CYP2D6, which is responsible for the metabolism of mCPP (12). Because nefazodone can inhibit its own metabolism (and that of its metabolites) and because the metabolism can be saturated, non-linear pharmacokinetics of the drug result. This manifests itself as significant inter- and intra-individual variation in standard drug pharmacokinetic parameters such as AUC and Cmax, meaning that titration of the drug dose is required to maximize efficacy while minimizing undesirable effects.

We have found that by preparing a formulation that provides for careful control of the absorption rate of nefazodone from an orally administered dose form, it is possible to avoid significant loss of bioavailability of the drug. This is contrary to typical expectation for the administration of a highly metabolized drug in an extended-release formulation. Also in a distinction from prior art for formulating extended-release dosage forms of arylpiperazine psychotropic agents as exemplified by buspirone in U.S. Pat. No. 5,431,922, no significant increase in bioavailability is seen either. This is advantageous, permitting one to avoid adjusting the dose when transferring from immediate-release to extended-release nefazodone formulations of the current invention. Control of absorption rate by means of the novel formulation also results surprisingly in a reduction of the metabolite mCPP, which may result in reduced frequency and intensity of undesirable effects following oral administration of nefazodone.

Drug Solubility

Nefazodone hydrochloride exhibits poor solubility in water, being defined as "sparingly soluble" under USP criteria. It has a dissociation constant (pKa=6.4) within the range of physiological pH, which means the solubility of this basic drug decreases further as pH is increased during transit from the stomach to the small intestine and colon. Therefore, the rate of release from a nefazodone extended-release dosage form cannot be controlled readily by oral formulation systems that rely on release of drug by diffusion. Matrix tablet systems based on hydrophobic polymers or waxy materials show a significant reduction in drug release as the pH of the release medium (including physiological fluids in vivo) increases to and exceeds the pKa value of nefazodone HCl. Conventional hydrogel matrix systems also behave in a similar manner and would face additional problems associated with the low water solubility of nefazodone HCl. These types of systems work well with more water soluble drugs, where drug release mechanism is based on diffusion of drug (in vitro and in vivo) from the hydrated matrix and can be more readily controlled by adjustment of viscosity and amount of polymer used in the formulation. Single polymer hydrophilic matrix systems based on non-ionic materials such as polyethylene oxide, high viscosity hydroxypropylmethylcellulose or hydroxypropylcellulose usually rely on diffusional control of release for drugs with adequate solubility in the physiological range. These systems are not readily adaptable to drugs with the solubility characteristics of nefazodone. Barrier coated pellet systems (for subsequent encapsulation or inclusion in tablet formulations) also work best with relatively water soluble drugs and are not suitable for nefazodone hydrochloride without using adjuvants in the formulation that enhance solubility of nefazodone in water. Such adjuvants would significantly increase the bulk of the formulation leading to unacceptably large tablets or capsules given the amount of nefazodone HCl required per dose.

Osmotic pump systems may not be readily adaptable for nefazodone because of the changing solubility with pH which may, in part, alter the osmotic driving force for drug release associated with solubility of the drug. Also, the total daily doses of nefazodone (200 to 600 mg) used in controlling the disorders for which the drug is effective may not be easily contained in a conveniently sized dosage form because of the levels of additional excipients these type of systems normally require for their functioning.

Using specific combinations of ionic and non-ionic gelling polymers, we have prepared pH-modulated hydrophilic matrix tablet formulations. These types of formulations are sensitive to the pH of the external environment and adjust their release rate in response to pH changes. As a result, these dosage forms control the release of nefazodone in vitro and in vivo in a way which overcomes the problems of preparing an extended-release formulation of nefazodone, with its low water solubility and with marked pH-dependent solubility in the physiological pH range.

Drug Doses

Nefazodone daily doses fall within the range of 200 to 600 mg for the twice daily, immediate-release systems. It could be possible to contain all but the uppermost end of this range in a single unit dosage form, especially if that were a tablet formulation, for some types of controlled-release system. A dosage form containing 400 to 500 mg of drug might be expected to weigh less than 1000 mg. However, as has been pointed out above, reducing the rate of nefazodone release into the gastrointestinal tract from a controlled-release dosage form might be expected to increase the extent of drug metabolism. This would mean that for nefazodone, formulated into many existing controlled-release systems, the amount of drug administered, in order to provide for plasma levels similar to the immediate-release formulation, would have to be increased. Increased drug amounts would require higher payloads for any delivery system and unit size would increase to an unacceptable point. As a result, the total daily dose would have to be provided within two or more dosage units. Furthermore, having to change total daily dose in switching from immediate-release nefazodone to the controlled-release formulation is undesirable as this can be confusing to the patient and difficult for the prescribing physician. A delivery system that could minimize the increase in extent of metabolism and/or loss of bioavailability resulting from a controlled-release formulation is therefore highly desirable.

The extended-release nefazodone formulation of the present invention employs a novel pH-modulated release mechanism. It can be distinguished from prior release-extending mechanisms such as described in U.S. Pat. No. 4,792,452 to Howard, et al. which involve pH-independent release.

Nefazodone has been disclosed previously in connection with a sustained-release oral dosage form. WO 97/47285 discloses delivery systems intended to release drug at a controlled rate in the stomach or upper intestine exclusively. Retention in the stomach is promoted by inclusion of a chemical agent that induces the stomach to function in the fed (as opposed to fasted) mode. Several classes of agents are disclosed as providing this effect including serotonin receptor antagonists, of which nefazodone is listed as one of the members of this class. In effect, nefazodone is not the active drug whose release is being controlled, but instead is included as an ingredient for its postulated effect on the stomach.

In summary, nothing in the prior art suggests the novel pH-modulated nefazodone extended-release formulations of the present invention. Specifically, overcoming the inherent difficulties presented with the metabolism, solubility and magnitude of dose characteristics of nefazodone, as well as maintaining comparable bioavailability of parent drug while reducing undesirable metabolite levels, underscores the novelty and inventive step associated with these new formulations.

SUMMARY OF THE INVENTION

It has been discovered that nefazodone can be orally administered in once-a-day extended-release (ER) dosage forms which contain nefazodone hydrochloride, ionic and non-ionic gelling polymers, an insoluble hydrophilic agent, and suitable amounts of one or more pharmaceutically acceptable excipients. By adjustment of the relative amounts of the ingredients, controlled-release of nefazodone in a pH-modulated manner is achieved. This release mechanism provides a means to overcome formulation problems associated with nefazodone's metabolism, solubility, and required dosage levels that prevented earlier development of an acceptable ER formulation for nefazodone.

DETAILED DESCRIPTION OF THE INVENTION

The present invention concerns pH-modulated controlled-release pharmaceutical formulations containing nefazodone hydrochloride as the active drug. These formulations, in turn, result in dosage forms and a method of orally administering nefazodone that have several advantages over immediate-release nefazodone systems. In addition, these new formulations of nefazodone permit use of acceptably-sized oral dosage forms to provide the total daily dose of nefazodone required. Results of in vivo dosing of the new nefazodone ER dosage forms indicate that no significant alternation of nefazodone content is required for ER dosing compared with nefazodone immediate-release dosing.

The pharmaceutical formulations employ a mixture of non-ionic polymers and ionic polymers along with an insoluble hydrophilic agent to encourage water penetration into the dosage form but not cause its ready disintegration. To control the rate of absorption of nefazodone the non-ionic polymer, ionic polymer and insoluble hydrophilic agent must be used in ratios that maintain required, though not necessarily similar, release rates of the drug at the different pH values found within the gastrointestinal tract. The dosage form must erode at a required rate to deliver nefazodone for absorption at an optimal rate as drug is released from the dosage form under the pH conditions prevalent in the intestine, principally by erosion of the mixture of polymers and insoluble hydrophilic agent.

In representative embodiments, extended-release oral dosage forms for nefazodone administration contain, in weight percents (wt %):

(a) about 33 to 45.5% nefazodone hydrochloride;

(b) about 16 to 33% of a non-ionic gelling polymer;

(c) about 10 to 21% of an ionic gelling polymer;

(d) about 16 to 22% of an insoluble hydrophilic agent; and (e) suitable amounts of one or more pharmaceutically acceptable excipients such as magnesium stearate for lubrication, a colorant, and the like.

The non-ionic gelling polymer is preferably hydroxypropylmethycellulose (HPMC) having a viscosity (for a 2% solution) in the range of about 3 to 1000 cps. Preferentially, the HPMC component is comprised of about 1 part by weight of 5 cps viscosity polymer and 2 parts by weight of 100 cps viscosity.

The ionic gelling polymer is a salt of alginic acid such as the potassium or, preferably, the sodium salt. The most preferred polymer is sodium alginate with a viscosity of about 9 cps (for a 1% solution).

The insoluble hydrophilic agent of preference is microcrystalline cellulose. In embodiments of the present invention magnesium stearate was employed as a lubricant and was present in about 0.2 to 1.5 wt %. Optionally, other pharmaceutically acceptable excipients could also be included.

The new nefazodone formulations can be used for preparation of unit dosage forms for oral administration. For example, tablets can be formed by compression. Such tablets can optionally be coated in standard fashion. A preferred coating would involve use of the aqueous-based proprietary film coat composition OPADRY white YS-1-18019.

Administration of the new nefazodone ER dosage forms provide advantages of convenience, improved patient compliance, a potential for lower incidence of adverse effects (due to decreased levels of m-chlorophenylpiperazine (M-CPP)), and lack of significant food effects on dosing.

The release rates of the new nefazodone formulations are different at different pH values; i.e., the system is pH-modulated rather than pH independent. This is a distinction from some prior art extended-release formulations for drugs of basic character like nefazodone which are formulated to have pH-independent drug release characteristics (for example U.S. Pat. No. 4,792,452, which uses sodium alginate and hydroxypropylmethylcellulose to achieve pH-independent rather than pH-modulated drug release). In those previous formulations we have found nefazodone pharmacokinetics to exhibit marked dependency on whether the dosage form is administered in the fed state or in the fasted state. Preferred formulations of the present invention release contained drug at the following rates in an in vitro dissolution test. The in vitro test employed is based on the apparatus described in the United States Pharmacopoeia, method 1 with media of various pH values being employed as shown in Table 1 below. The stirring speed was 200 rpm. The amount of drug released into the dissolution medium at the listed time-points was determined by UV spectroscopy.

TABLE 1

| | Time (hours) | Cumulative % Nefazodone Released |
|---|---|---|
| pH 2.0 | 0.5 | 3 to 12 |
| | 1 | 7 to 16 |
| | 2 | 15 to 22 |
| | 4 | 20 to 35 |
| | 6 | 24 to 50 |
| | 8 | 35 to 70 |

TABLE 1-continued

| | Time (hours) | Cumulative % Nefazodone Released |
|---|---|---|
| | 12 | 45 to 90 |
| | 16 | 52 to 100 |
| pH 4.5 | 0.5 | 5 to 18 |
| | 1 | 10 to 22 |
| | 2 | 15 to 38 |
| | 4 | 20 to 65 |
| | 6 | 25 to 85 |
| | 8 | 40 to 95 |
| | 12 | 55 to 100 |
| | 16 | 65 to 100 |
| pH 6.8 | 0.5 | 8 to 22 |
| | 1 | 16 to 48 |
| | 2 | 30 to 70 |
| | 4 | 55 to 100 |
| | 6 | 75 to 100 |
| | 8 | 85 to 100 |

Nefazodone ER dosage forms of this invention, e.g. as described in the Specific Embodiments, liberate their contained drug at rates slower than immediate-release nefazodone formulations but at rates which provide for the desired plasma concentration-time curve, wherein there is not a remarkable reduction in bioavailability as might be anticipated with typical extended-release systems.

For comparative purposes, a controlled-release reference formulation of nefazodone (nefazodone-CR) based on non-ionic gelling polymers along with typical tablet excipients was prepared having a composition as shown below:

Standard Controlled-release Nefazodone Reference Formulation (Nefazodone CR)

| Ingredient | Quantity per Tablet |
|---|---|
| Hydroxypropylcellulose NF | 75 mg |
| Hydroxypropylmethylcellulose 2208 NF, 4000 cps grade | 100 mg |
| Nefazodone hydrochloride | 400 mg |
| Povidone USP | 20 mg |
| Magnesium stearate NF | 5 mg |

Either this standard nefazodone CR formulation, or the marketed immediate-release nefazodone formulation, was administered to human volunteers on a once daily basis both under fasted and fed conditions. Serial plasma samples were taken at appropriate intervals and analyzed for nefazodone. The standard controlled-release formulation of nefazodone showed a relative bioavailability of 28% (compared with the immediate-release formulation). Furthermore, this formulation also exhibited a marked food effect, with the relative bioavailability increasing to 66% when taken with a high fat meal. (See Table 2)

TABLE 2

Mean Pharmacokinetic Parameters of Nefazodone from Example Standard CR Formulation

| | Cmax (ng/ml) | AUC (ng.hr/ml) | Relative bioavailability (%)* |
|---|---|---|---|
| Fasted | 130.8 | 1496 | 28 |
| Fed | 575.3 | 3514 | 66 |

*relative to same dose of immediate-release nefazodone formulation (in a single dose study)

This is an important result as a patient stabilized in a regimen using such a controlled-release dosage form administered in the fasted state might experience peak plasma drug concentration-related side effects if the administration was altered by the medication being taken with food. Conversely, a patient stabilized in a regimen based on such a dosage form being administered in the fed state might experience failure of therapy if the patient switched to taking the medication without food.

The development of an extended-release pharmaceutical formulation often involves a hydrophilic polymer matrix system. These formulations tend to involve uncomplicated, inexpensive manufacturing processes, but previous experience, based on prior art approaches, has shown that these types of formulations exhibit significant effects on drug pharmacokinetics. Large variations in PK parameters arise depending on whether the formulation is given with food or not Such food effects can lead to inconvenience in establishing dosing regimens for patients.

Hydrophilic matrix extended-release formulations of a drug of low solubility, such as nefazodone HCl, and providing for reproducible behavior irrespective of whether the drug is taken with food or without food are, in general, extremely difficult to formulate. The mechanism of drug release for formulations utilizing these delivery systems is principally one of erosion of the matrix. Thus, a notable food effect might be expected, although its relative magnitude will depend on various physicochemical properties of the drug substance in question. For example, nifedipine (defined as being practically insoluble in water in the USP) was shown to exhibit a notable food effect when administered as a hydrophilic matrix extended-release formulation (Abrahamsson et al., *J. Controlled Release*, 1998, 52, 301–310). The area under the curve (AUC) increased by 75%, relative to data obtained in the fasted state, when the nifedipine hydrophilic matrix extended-release formulation was dosed in the fed state.

A pH modulated extended-release nefazodone formulation (nefazodone ER) according to the current invention (200 mg per dosage unit) given in the fasted state was compared in human volunteers with conventional immediate-release nefazodone (nefazodone IR: 100 mg per dosage unit) given in the fasted state as two separate doses 12 hours apart. Analysis of drug and metabolites in the plasma of the volunteers after administration of the drug allowed the following pharmacokinetic parameters to be determined as shown in Table 3.

TABLE 3

Nefazodone Pharmacokinetic Parameters: ER v. IR

Extended-release nefazodone (200 mg dose given a.m.):

|  | Cmax (ng/ml) | tmax (hours) | AUC (h.ng/ml) | F (%)* |
|---|---|---|---|---|
| Nefazodone | 195 | 5 | 1267 | 77 |
| hydroxy-nef | 65 | 5 | 352 | 54 |
| Dione | 453 | 4 | 5699 | 55 |
| mCPP | 16 | 5 | 114 | 50 | immediate-release nefazodone (100 mg dose):

|  | Cmax (ng/ml) | tmax (hours) | AUC (h.ng/ml) |
|---|---|---|---|
| Nefazodone | 310 | 2 | 1627 |
| hydroxy-nef | 97 | 2 | 642 |
| Dione | 710 | 2 | 10617 |
| mCPP | 24 | 2 | 259 |

*relative to the immediate-release formulation

The pH modulated extended-release system (nefazodone ER) can be seen to be acting to control drug absorption in vivo. Times to maximum values for plasma concentrations are delayed relative to the conventional formulation. The maximum plasma level is blunted significantly (note we are comparing 200 mg of the ER to 100 mg IR and the peak level for the 200 mg ER dose is 60 to 70% of that for 100 mg of the IR formulation). This may be beneficial if the occasional difficulties in tolerance to the drug during the initial dosing period are associated with peak plasma levels. The blunting of peak plasma levels seen with the ER formulation would allow dosing to commence at higher doses than when initiating therapy with the IR product and will enable titration to an effective dose with fewer titration steps than with the IR product.

Maintenance of the bioavailability levels of nefazodone in combination with a reduction in metabolite levels for the ER formulation is contrary to expectation for a heavily metabolized drug formulated as an extended-release system. The reasonable maintenance of plasma levels of hydroxynefazodone and the dione metabolite (50–60% of the levels seen with the immediate-release tablet) might be important as these active metabolites might contribute to therapeutic efficacy. The reduction in levels of mCPP relative to the immediate-release formulation (25% of Cmax and 20% of AUC relative scaled directly to correct for dose differences) might be beneficial as this metabolite may be associated with some of the undesirable effects of nefazodone.

A comparative pharmacokinetic study in fed and fasted subjects was carried out employing a new nefazodone ER formulation (example 1). A remarkable and unexpected lack of a food effect was observed in contrast to what is seen with the standard conventional controlled-release nefazodone formulation. (See Table 4)

TABLE 4

Food Effect: Nefazodone ER v. Standard CR Nefazodone

Nefazodone - ER

| Parameter | |
|---|---|
| cMax (ng/ml) | |
| -with food | 195 |
| -without food | 157 |
| AUC (ng.h/ml) | |
| -with food | 1236 |
| -without food | 1234 |

The standard extended-release formulation (400 mg dose) gave the following data:

Nefazodone - CR

| Parameter | |
|---|---|
| cMax (ng/ml) | |
| -with food | 575 |
| -without food | 131 |
| AUC (ng.h/ml) | |
| -with food | 3514 |
| -without food | 1496 |

This lack of effect with the novel formulation described in example 1 provides convenience in terms of avoiding restrictions on how patients may be obliged to take their medication around mealtimes.

The nature of the formulation and the pH-modulated extended-release of nefazodone seen in in vitro experiments and the resultant in vivo drug release characteristics are important to the performance observed in terms of drug and metabolite levels, pharmacokinetic parameter values, and the lack of a food effect.

Typical formulations having the desired characteristics are described below.

In general, the present invention provides improved formulations for the oral administration of nefazodone, or a pharmaceutically acceptable salt, e.g. the hydrochloride salt, thereof. The improved formulations provide controlled/extended-release of nefazodone requiring from about 4 to 16 hours for complete drug release as measured using standard in vitro dissolution protocols employing test media in the pH 1.2 to 7.0 range. Typically, about 50% of the nefazodone should be released at 4 hours and about 85% at 8 hours at pH 7.0. Release rates are slower at lower pH values. These measurements are made using USP type 1 apparatus in vitro test conditions with a stirring speed of 200 rpm.

These improved controlled/extended-release oral pharmaceutical formulations containing nefazodone or a pharmaceutically acceptable salt thereof are characterized by:

1. requiring from 4 to 6 hours for virtually complete drug release as measured with standard in vitro testing at pH values in the 1.2 to 7.0 range;

2. nefazodone levels that are extended, relative to those seen with the immediate release formulation, and that are maintained at or above therapeutic levels for up to 24 hours;

3. providing reduced levels of nefazodone metabolites, particularly mCPP, but retaining similar levels of nefazodone itself compared to oral administration with immediate-release formulations; and 4. lacking a significant food effect on dosing.

PREFERRED EMBODIMENTS

Unless stated otherwise, all percentages given below are weight percents, based on total composition weight. All disclosures and references referred to herein are hereby incorporated by reference.

EXAMPLE 1

Nefazodone hydrochloride (130 g) was blended with 65 g sodium alginate (9 cps grade, for example Manucol LD, Monsanto Performance Materials, Surrey, U.K.), 35.8 g hydroxypropylmethylcellulose 2208 USP 100 cps grade, 16.25 g of hydroxypropylmethylcellulose 2910 USP 5 cps grade and 65.13 g of microcrystalline cellulose NF for fifteen minutes in a suitable mixer. The drug\excipient blend was lubricated by addition of 4.8 g of magnesium stearate NF and mixing for a further five minutes. The resulting lubricated blend was compressed into tablets each weighing 485 mg and containing 200 mg of nefazodone hydrochloride. The finished tablets were coated with an aqueous-based proprietary film coat composition Opadry white YS-1-18019.

EXAMPLE 2

Nefazodone hydrochloride (400 g) was blended in a planetary mixer with 200 g sodium alginate (9 cps grade), 110 g hydroxypropylmethylcellulose 2208 USP 100 cps grade, 50 g of hydroxypropylmethylcellulose 2910 USP 5 cps grade and 100.2 g of microcrystalline cellulose NF. To this mixture 6.4 g magnesium stearate NF was added and the blend further mixed for five minutes. The mixture was passed through a roller compactor and the resultant ribbons of compacted material were passed through an oscillating granulator to produce free flowing granules. These granules were mixed with 100.2 g of microcrystalline cellulose in a planetary mixer. The product from this operation was lubricated by mixing with a further 3.2 g of magnesium stearate NF, operating the planetary mixer for a further three minutes after the addition of the magnesium stearate. This final blend was compressed into tablets each containing 200 mg of nefazodone hydrochloride.

EXAMPLE 3

Sodium alginate 9 cps grade (80 g), 90 g of hydroxypropylmethylcellulose 2208 USP 100 cps grade, 200 g nefazodone hydrochloride and 100.3 g of microcrystalline cellulose USP were passed through an 800 micron aperture wire mesh screen into a planetary mixer bowl and the mixer operated for ten minutes. The screened blend was mixed with 1.6 g magnesium stearate NF for ten minutes. The mixture was passed through a roller compactor and the resultant ribbons of compacted material were passed through an oscillating granulator to produce free flowing granules. These granules were further mixed with 1.3 g magnesium stearate NF, employing a planetary mixer for three minutes. The final lubricated granules were compressed into tablets each containing 200 mg nefazodone hydrochloride.

EXAMPLE 4

Nefazodone hydrochloride (437 g), 109.2 g sodium alginate 9 cps grade, 229.4 g hydroxypropylmethylcellulose 2208 USP 100 cps grade and 219.4 g microcrystalline cellulose NF were passed through an 800 micron aperture wire mesh screen into a planetary mixer bowl and blended for ten minutes. Magnesium stearate NF (3.32 g) was added to the contents of the mixer bowl, passing this through a 500 micron aperture mesh screen. The mixer was operated for a further three minutes to incorporate the magnesium stearate into the blend. This mixture was passed through a roller compactor and the resultant ribbons of compacted material were size reduced in an oscillating granulator to produce free flowing granules. These granules were further mixed with an additional 6.73 g of magnesium stearate NF. The final lubricated granules were compressed into tablets each containing 400 mg of nefazodone hydrochloride.

EXAMPLE 5

Nefazodone hydrochloride (165 g), 82.5 g sodium alginate 9 cps grade, 132 g hydroxypropylmethylcellulose 2208 NF 100 cps grade, 33 g hydroxypropylmethylcellulose 2910 NF 5 cps grade and 82.7 g microcrystalline cellulose NF were mixed together in a small mixer for ten minutes. Magnesium stearate NF (4 g) was added to the blend with a further three minutes mixing. The resultant mixture was compressed into tablets each containing 100 mg of nefazodone hydrochloride.

EXAMPLE 6

Hydroxypropylmethylcellulose 2208 NF 100 cps grade (90 g), 225 g nefazodone hydrochloride, 75 g sodium alginate 9 cps grade and 107.5 g microcrystalline cellulose NF were blended together in a small mixer for ten minutes. Magnesium stearate NF (5 g) was added and the mixer operated for a further three minutes. This blend was compressed into tablets each containing 300 mg nefazodone hydrochloride.

EXAMPLE 7

Nefazodone hydrochloride (177 g), 85.5 g sodium alginate 9 cps grade, 141.6 g hydroxypropylmethylcellulose 2208 USP 100 cps grade and 88.7 g microcrystalline cellulose NF were blended together in a small mixer before adding 4 g magnesium stearate NF and mixing to incorporate this into the blend. This final mixture was incorporated into tablets each containing 100 mg nefazodone hydrochloride.

Reasonable variations, such as those that would occur to one of ordinary skill in the art, can be made herein without departing from the scope of the invention.

Drug release data from in vitro testing is shown for each of the above examples in Tables 5 to 11. The in vitro dissolution testing was conducted using USP apparatus 2, with rotor speed at 200 rpm; employing media pH of 2.0; 4.5; and 7.0. Nefazodone concentrations in the dissolution media were determined by UV spectroscopy.

TABLE 5

In Vitro Release Data for Nefazodone from Formulation Described in Example 1

|  | Time (hours) | % Nefazodone Released |
|---|---|---|
| pH 2.0 | 1 | 11 |
|  | 2 | 18 |
|  | 3 | 23 |
|  | 4 | 28 |
|  | 6 | 38 |
|  | 8 | 50 |
|  | 10 | 59 |
|  | 12 | 67 |
|  | 15 | 80 |
| pH 4.5 | 1 | 22 |
|  | 2 | 36 |
|  | 3 | 48 |
|  | 4 | 59 |
|  | 6 | 78 |
|  | 8 | 93 |
|  | 10 | 100 |
| pH 7.0 | 1 | 39 |
|  | 2 | 67 |
|  | 3 | 86 |
|  | 4 | 100 |
|  | 6 | 100 |

TABLE 6

In Vitro Release Data for Nefazodone from Formulation Described in Example 2

|  | Time (hours) | % Nefazodone Released |
|---|---|---|
| pH 1.2 | 1 | 11 |
|  | 2 | 18 |
|  | 4 | 31 |
|  | 6 | 44 |
|  | 8 | 56 |
|  | 12 | 74 |
|  | 16 | 90 |
| pH 4.5 | 1 | 14 |
|  | 2 | 27 |
|  | 4 | 51 |
|  | 6 | 71 |
|  | 8 | 83 |
|  | 12 | 97 |
|  | 16 | 99 |
| pH 7.0 | 1 | 36 |
|  | 2 | 64 |
|  | 4 | 96 |
|  | 6 | 100 |
|  | 8 | 100 |

TABLE 7

In Vitro Release Data for Nefazodone from Formulation Described in Example 3

|  | Time (hours) | % Nefazodone Released |
|---|---|---|
| pH 2.0 | 1 | 11 |
|  | 2 | 19 |
|  | 4 | 34 |
|  | 6 | 49 |
|  | 8 | 63 |
|  | 12 | 82 |
|  | 16 | 92 |
| pH 4.5 | 1 | 12 |
|  | 2 | 24 |
|  | 4 | 46 |
|  | 6 | 65 |
|  | 8 | 77 |
|  | 12 | 91 |
|  | 16 | 97 |
| pH 7.0 | 1 | 24 |
|  | 2 | 45 |
|  | 4 | 75 |
|  | 6 | 98 |
|  | 8 | 100 |

TABLE 8

In Vitro Release Data for Nefazodone from Formulation Described in Example 4

|  | Time (hours) | % Nefazodone Released |
|---|---|---|
| pH 4.5 | 1 | 15 |
|  | 2 | 28 |
|  | 4 | 52 |
|  | 6 | 72 |
|  | 8 | 88 |
|  | 12 | 98 |
|  | 16 | 99 |
| pH 7.0 | 1 | 24 |
|  | 2 | 47 |
|  | 4 | 82 |
|  | 6 | 103 |
|  | 8 | 105 |

TABLE 9

In Vitro Release Data for Nefazodone from Formulation Described in Example 5

|  | Time (hours) | % Nefazodone Released |
|---|---|---|
| p/H 4.5 | 1 | 16 |
|  | 2 | 32 |
|  | 4 | 58 |
|  | 6 | 78 |
|  | 8 | 92 |
|  | 12 | 99 |
|  | 16 | 99 |
| pH 7.0 | 1 | 21 |
|  | 2 | 43 |
|  | 4 | 81 |
|  | 6 | 98 |
|  | 8 | 99 |

TABLE 10

In Vitro Release Data for Nefazodone from Formulation Described in Example 6

|  | Time (hours) | % Nefazodone Released |
|---|---|---|
| pH 4.5 | 1 | 20 |
|  | 2 | 33 |
|  | 4 | 57 |
|  | 6 | 76 |
|  | 8 | 90 |
|  | 12 | 101 |
|  | 16 | 103 |
| pH 7.0 | 1 | 27 |
|  | 2 | 47 |
|  | 4 | 80 |
|  | 6 | 99 |
|  | 8 | 102 |

TABLE 11

In Vitro Release Data for Nefazodone from Formulation Described in Example 7

|  | Time (hours) | % Nefazodone Released |
|---|---|---|
| pH 4.5 | 1 | 16 |
|  | 2 | 31 |
|  | 4 | 58 |
|  | 6 | 78 |
|  | 8 | 91 |
|  | 12 | 101 |
|  | 16 | 102 |
| pH 7.0 | 1 | 27 |
|  | 2 | 53 |
|  | 4 | 89 |
|  | 6 | 105 |
|  | 8 | 106 |

EXAMPLE 8

Tablets containing 200 mg nefazodone hydrochloride prepared in accord with either example 2 (treatment A) or example 3 (treatment B) were administered to two groups of human volunteers on a once daily basis for six days. The pooled groups of volunteers also received 100 mg immediate-release nefazodone tablets on a b.i.d. basis for six days in a separate leg of the study. Analysis of nefazodone hydrochloride and its metabolites in plasma drawn on day six at appropriate time intervals was undertaken. The following data was found and is expressed in Table 12 as nanograms/mL (standard deviation).

TABLE 12

In Vivo Release Data (Nefazodone and Metabolites): Formulation Comparison

| Time (hours) | IR formulation | ER treatment A | ER treatment B |
|---|---|---|---|
| 0 | 79.47 (57.73) | 101.0 (83.72) | 88.45 (41.97) |
| 0.5 | 675.76 (385.60) | 156.3 (124.65) | 109.32 (50.06) |
| 1.0 | 610.65 (243.04) | 241.77 (223.84) | 139.82 (46.76) |
| 2 | 423.3 (197.83) | 338.03 (253.68) | 229.82 (70.71) |
| 2.5 | 462.88 (188.98) |  |  |
| 3 | 348.16 (173.38) | 366.58 (311.69) | 267.54 (84.83) |
| 3.5 |  | 317.61 (233.08) | 263.07 (83.79) |
| 4 | 281.97 (153.41) | 273.99 (206.99) | 223.74 (63.51) |
| 4.5 |  | 275.86 (179.64) | 249.19 (95.53) |
| 5 |  | 250.83 (187.64) | 211.05 (64.63) |
| 6 | 185.82 (121.34) | 211.24 (166.35) | 175.01 (66.95) |
| 8 | 111.08 (70.90) | 154.57 (118.98) | 144.5 (67.24) |
| 10 |  | 135.82 (130.35) | 118.95 (46.52) |
| 12 | 55.33 (43.08) | 125.6 (97.39) | 113.12 (53.29) |
| 12.5 | 141.86 (114.90) |  |  |
| 13 | 273.15 (205.70 |  |  |
| 14 | 350.55 (137.79) | 133.54 (105.68) | 116.89 (75.58) |
| 14.5 | 299.85 (174.61) |  |  |
| 15 | 278.84 (145.58) |  |  |
| 16 | 247.49 (156.29) | 115.62 (87.11) | 115.09 (84.21) |
| 20 | 123.19 (92.64) | 79.63 (49.00) | 73.32 (37.99) |
| 24 | 97.11 (54.81) | 92.44 (57.31) | 59.48 (59.48) |

The results obtained clearly show that at steady state the novel formulations that are the subject of this invention demonstrate excellent extended-release properties. It is particularly significant to demonstrate this effect for nefazodone, a drug whose pharmacokinetic properties on multiple dose administration are difficult to predict from data arising from single dose administration studies. Additionally ER treatment A was evaluated in patients dosed in the fed state and showed the same bioavailability relative to an immediate-release formulation as that seen in the fasted state. This has clear benefit in flexibility of dosing.

REFERENCES

1) Greene, D., Barbhaiya, R. (1997) *Clin. Pharmacokinet.,* 33, 260–275
2) Mayol, R. F., Cole, C. A., Luke, G. M., et al. (1994) *Drug Metab. Dispos.* 22, 304–311
3) Robinson, J. R., Lee, V. H. L. (1987) *Controlled Drug Delivery: Fundamentals and Applications*, Marcel Dekker Inc., USA
4) Kennett, G. A., Curzon, G (1991) *Brit. J. Pharmacol.,* 103, 2016–2020
5) Murphy, D. L., Lesch, K. P., Aulakh, C. S., Pigott, T. A. (1991) *Pharmacol. Rev.,* 43, 527–552
6) Baxter, G. G., Kennett, G. A., Blanney, F., Blackburn, T. (1995) *Trends Pharmacol. Sci.,* 16, 105–110
7) Kennett, G. A., Wood, M. D., Glen, A., Grewal, S., Forbes, J., Gadre, A., Blackburn, T. P. (1994) *Brit. J. Pharmacol.,* 111, 797–802
8) Kennett, G. A., Whitton, P., Shah, K., Curzon, G. (1989) *Eur. J. Pharmacol.,* 164, 445–454
9) Kennett, G. A. (1993) Curr. Opin. Invest. Drugs, 2, 317–362
10) Sugimoto, Y., Yamada, J., Yoshikawa, T., Horisaka, K. (1996) *Eur. J. Pharmacol.,* 307, 75–80
11) Kaul, S., Shukla, U. A., Barbhaiya, R. H. (1995) *J. Clin. Pharmacol.,* 35, 830–834
12) Barbhaiya, R. H., Buch, A. B., Greene, D. S. (1996) *Brit. J. Clin. Pharmacol.,* 42, 573–81

What is claimed is:

1. A pH-modulated extended release pharmaceutical formulation for the oral administration of nefazodone or a pharmaceutically acceptable salt thereof, wherein the improvements comprise:

(a) requiring from about 4 to 16 hours for essentially complete drug release from the formulation as measured using standard USP in vitro dissolution protocols employing test media in the pH 1.2 to 7.0 range;

(b) providing, after oral administration, extended blood levels of nefazodone relative to blood levels seen with immediate release formulations and these extended levels are maintained at or above therapeutic levels for up to 24 hours;

(c) providing, after oral administration, reduced amounts of nefazodone metabolites, particularly mCPP, while maintaining the blood levels of nefazodone at concentrations comparable to those seen following oral administration with immediate-release formulations; and (d) lacking a significant food effect on oral administration.

2. The improved formulation of claim 1 wherein the controlled/extended-release formulation is selected from the group consisting of nefazodone HCl embedded in a matrix; formed into micropellets; or formed into coated micropellets.

3. A pharmaceutical formulation useful for making an oral extended-release nefazodone pH-modulated dosage form comprising:

(a) from about 33 to 45.5 wt % nefazodone hydrochloride;

(b) from about 16 to 33 wt % of a non-ionic gelling polymer;

(c) from about 10 to 21 wt % of an ionic gelling polymer; and (d) from about 16 to 22 wt % of an insoluble hydrophilic agent.

4. The pharmaceutical formulation of claim 3 further containing suitable amounts of one or more pharmaceutically acceptable excipients.

5. The formulation of claim 4 wherein the excipient component includes at least one of: colorant, colloidal silica, and magnesium stearate.

6. The formulation of claim 4 wherein the excipient component contains from about 0.2 to 1.5 wt % of magnesium stearate.

7. The formulation of claim 3 wherein the non-ionic gelling polymer (b) is hydroxypropylmethylcellulose.

8. The formulation of claim 3 wherein the ionic gelling polymer (c) is sodium alginate.

9. The formulation of claim 3 wherein the insoluble hydrophilic agent (d) is microcrystalline cellulose.

10. The formulation of claim 7 wherein the hydroxypropylmethylcellulose has a viscosity from about 3 to 1000 cps.

11. The formulation of claim 4 comprising:

(a) from about 40 to 45 wt % nefazodone hydrochloride;

(b) from about 16 to 20 wt % of hydroxypropylmethylcellulose;

(c) from about 19 to 22 wt % of sodium alginate;

(d) from about 19 to 22 wt % of microcrystalline cellulose; and (e) from about 1 to 1.5 wt % of magnesium stearate.

12. The formulation of claim 11 wherein the hydroxypropylmethylcellulose component is comprised of about one part 5 cps to two parts 100 cps viscosity.

13. An oral dosage form comprising the pharmaceutical formulation of claim 1.

14. An oral dosage form comprising the pharmaceutical formulation of claim 3.

15. An oral dosage form comprising the pharmaceutical formulation of claim 4.

16. An oral dosage form comprising the pharmaceutical formulation of claim 11.

17. The oral dosage form of claim 13 in the form of a film-coated tablet.

18. The oral dosage form of claim 14 in the form of a film-coated tablet.

19. The oral dosage form of claim 15 in the form of a film-coated tablet.

20. The oral dosage form of claim 16 in the form of a film-coated tablet.

21. An improved method for administering nefazodone comprising administration of the pharmaceutical formulations of claim 1.

22. An improved method for administering nefazodone comprising administration of the pharmaceutical formulations of claim 2.

23. An improved method for administering nefazodone comprising administration of the pharmaceutical formulations of claim 3.

24. An improved method for administering nefazodone comprising administration of the pharmaceutical formulations of claim 4.

25. An improved method for administering nefazodone comprising administration of the pharmaceutical formulations of claim 11.

* * * * *